(12) United States Patent
Garrison

(10) Patent No.: US 6,609,911 B2
(45) Date of Patent: Aug. 26, 2003

(54) DENTAL CLAMP

(76) Inventor: John E. Garrison, 15800 Ridge La., Spring Lake, MI (US) 49456

( * ) Notice: Subject to any disclaimer, the term of this patent is extended or adjusted under 35 U.S.C. 154(b) by 0 days.

(21) Appl. No.: 09/682,905

(22) Filed: Oct. 31, 2001

(65) Prior Publication Data

US 2002/0061492 A1 May 23, 2002

Related U.S. Application Data

(60) Provisional application No. 60/244,936, filed on Nov. 1, 2000.

(51) Int. Cl.[7] ................................................. A61C 5/12
(52) U.S. Cl. ...................................................... 433/139
(58) Field of Search ............................................ 433/139

(56) References Cited

U.S. PATENT DOCUMENTS

| 412,622 A | 10/1889 | Ivory | 433/139 |
|---|---|---|---|
| 1,336,746 A | 4/1920 | Ivory | 433/139 |
| 1,520,753 A | * 12/1924 | Ivory | 433/139 |
| 4,007,530 A | 2/1977 | Gaccione | 433/139 |
| 4,265,623 A | 5/1981 | Soelberg et al. | 433/139 |
| 4,639,221 A | 1/1987 | Sairenji | 433/139 |
| 4,986,752 A | 1/1991 | Graves | 433/139 |
| 5,342,197 A | 8/1994 | Stein et al. | 433/155 |
| 5,503,556 A | 4/1996 | Leonard et al. | 433/139 |
| 6,293,796 B1 | 9/2001 | Trom et al. | 433/155 |

* cited by examiner

*Primary Examiner*—John J. Wilson
(74) *Attorney, Agent, or Firm*—McGarry Bair PC

(57) ABSTRACT

A dental clamp for supporting a flexible sheet around a tooth during a dental operation has a resilient member connecting oppositely disposed jaws. The resilient member biases the jaws toward each other. A plurality of resilient fingers extend toward each other from each jaw.

19 Claims, 4 Drawing Sheets

DENTAL CLAMP

CROSS REFERENCE TO RELATED APPLICATIONS

This application claims the benefit of U.S. Provisional Application Ser. No. 60/244,936 filed Nov. 1, 2000.

BACKGROUND OF INVENTION

1. Field of the Invention

The invention relates to a dental clamp and, more particularly, to a clamp for use with a rubber dam when it is desirable to isolate one or more teeth being treated.

2. Description of the Related Art

Certain dental operations, such as root canals, are performed with a flexible sheet, such as a rubber dam retained around the tooth, or in some cases several teeth, undergoing treatment. The dam isolates one or more teeth from the rest of the interior of the patient's mouth and serves two functions. One, it prevents ingestion by the patient of medicine or other substances associated with the operation and, two, it inhibits the introduction of bacteria and other contaminants from the mouth into the operating theater around the tooth during the procedure. The dam comprises a flexible membrane retained in a frame. While the frame is placed outside the mouth, the membrane is flexible enough to extend inwardly of the patient's mouth. In the case of a single treated tooth, a hole is punched in the membrane to accommodate the tooth and the dam is inserted over the tooth so that it is the only tooth exposed through the hole. A similar procedure is employed if more than one tooth is to be isolated.

A dental clamp is typically used to retain the rubber dam in proper position around the tooth. Dental clamps include a pair of laterally opposed jaws that are spring-biased to grip the tooth immediately above the gum line. The clamp typically attaches to the dam at the hole for positioning the dam around the tooth. The clamp is applied by spreading the jaws with a special forceps, positioning the clamp around the tooth, and carefully releasing the jaws when the clamp has been properly placed. The edges of the jaws may include serrations to facilitate gripping of the tooth or it may include a soft bumper to avoid damage to the surrounding gums.

FIG. 1 shows one embodiment of a tooth clamp according to the prior art. The tooth clamp comprises a resilient arcuate spring A which is attached at each end to jaws B. The jaws B are laterally opposed and define an intervening space C. The inwardly directed edge D of each jaw B is curved and may include serrations. The shape of the edge D is intended to correspond roughly with the arc of a tooth along the gum line.

Each jaw B is provided with an aperture F for insertion of a forceps, which is used to spread the jaws B apart for placement of the clamp around the tooth. Tabs E extend laterally from the outside edges of the jaws B. The tabs E are inserted into a hole in a rubber dam G to spread the hole open.

One of the problems with known clamps is that the spring force, and thus the force required to open the clamp, is very high, making the placement of the clamp on a tooth difficult. Also, such force may cause the device to bite into the gums if the placement is improper, or if the device is urged downwardly by the shape of the tooth. In addition, the clamp may slide off the tooth during a procedure, thus disrupting the treatment and permitting the introduction of contaminating substances to the operating theater.

SUMMARY OF INVENTION

These problems are solved by the present improvement in a dental clamp of the type for clamping a tooth and supporting a flexible sheet during a dental operation. Such a clamp typically has a resilient member connecting oppositely disposed jaws and biasing the jaws toward each other. Each jaw comprises a plate having an outward edge for engaging the flexible sheet and an inward edge that together with the opposing inward edge define a space between the jaws. The improvement lies in a plurality of resilient fingers extending from the inward edge of each plate and toward the oppositely disposed plate.

Preferably, the resilient fingers are arranged in a rank on each jaw. In one aspect of the invention, the resilient fingers extend slightly away from the resilient member. In another aspect of the invention, each finger has a crimp to facilitate resiliency. Preferably, the ends of the fingers are arranged to define a curve roughly approximating the curvature of a tooth. The jaws can each incorporate an additional tab to further engage and hold the flexible sheet.

DETAILED DESCRIPTION

Figure 1:
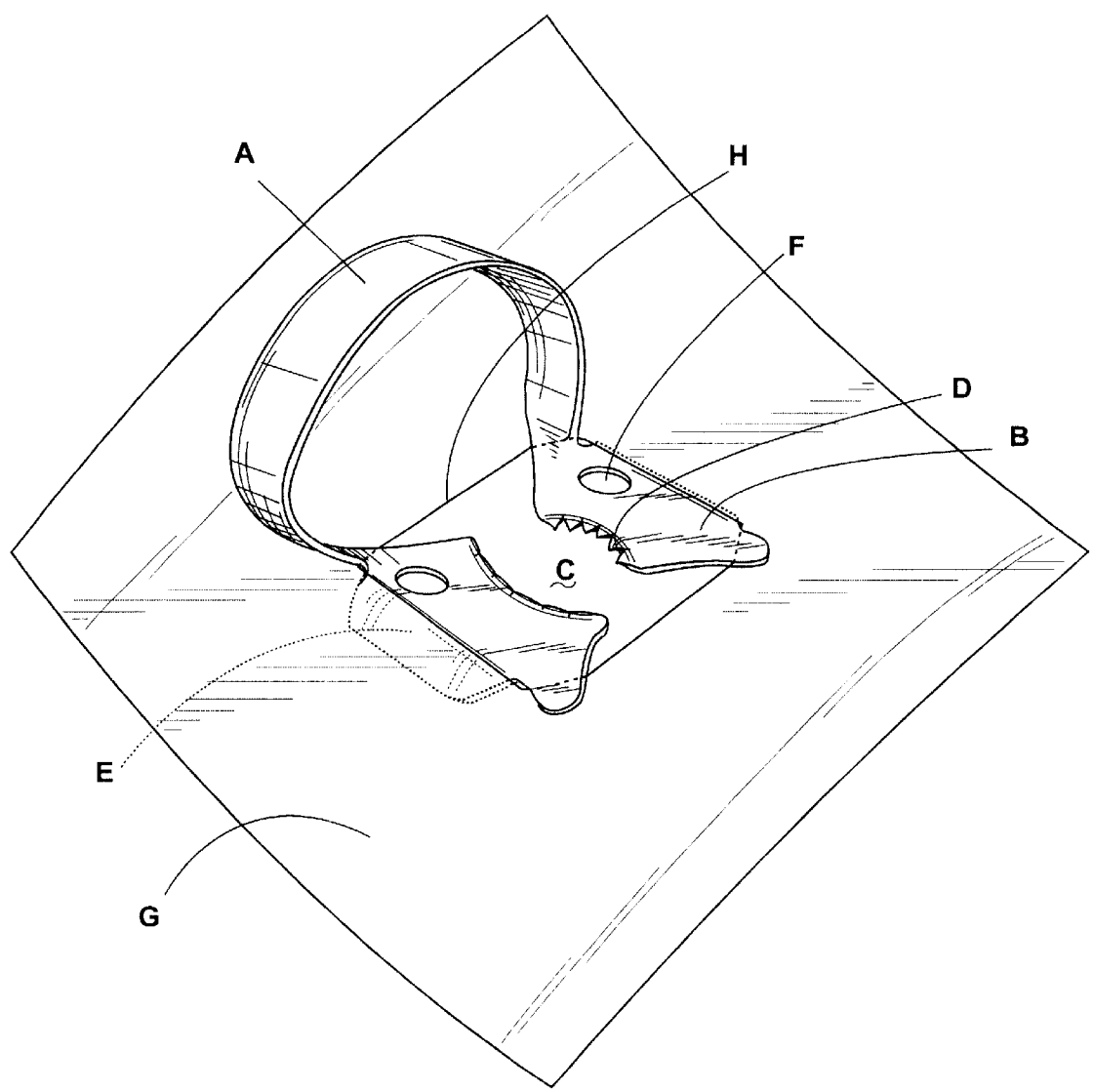
FIG. 1 is a perspective view of a tooth clamp according to the prior art.
Figure 2:
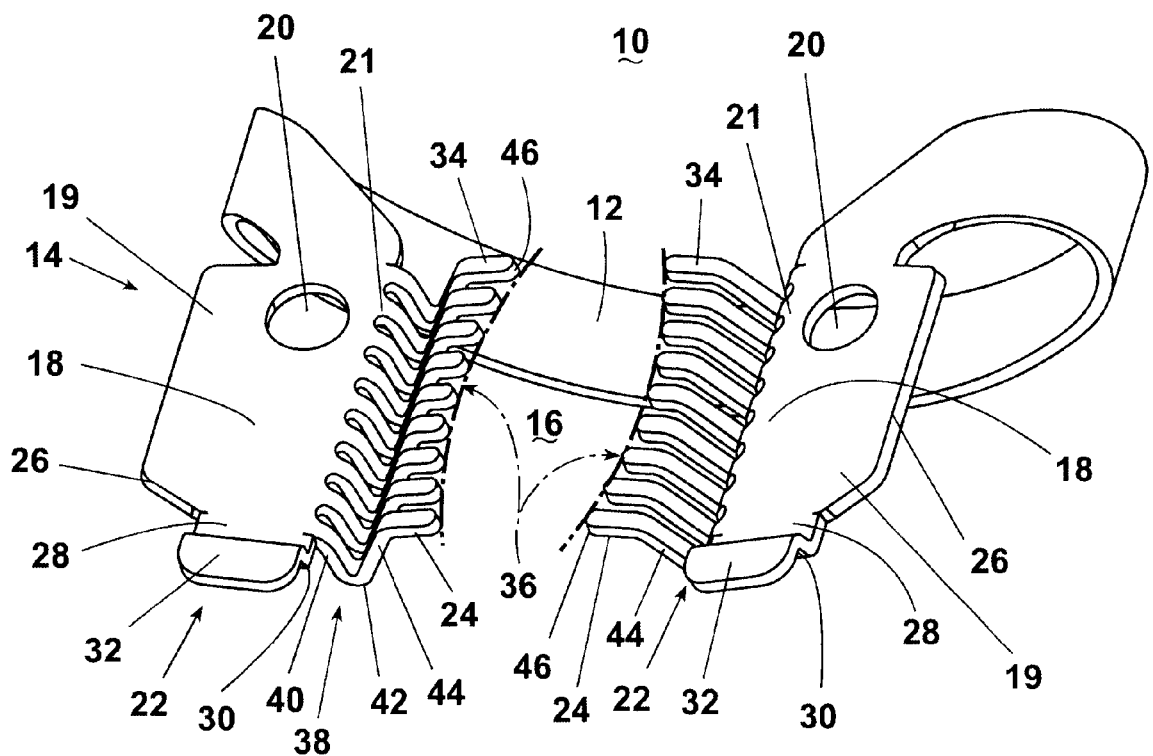
FIG. 2 is a perspective view from the underside of a tooth clamp according to the invention.

An embodiment of the invention is illustrated in FIG. 2, where a dental clamp 10 according to the invention comprises a resilient arcuate bridge 12 connecting a pair of opposing jaws 14. The bridge 12 is configured to extend over the teeth when the clamp 10 has been properly installed. The jaws 14 define a space 16 therebetween. Each jaw 14 comprises a plate 18 with an aperture 20 therethrough, a dam tab 22, and resilient fingers 24.

Figure 3:
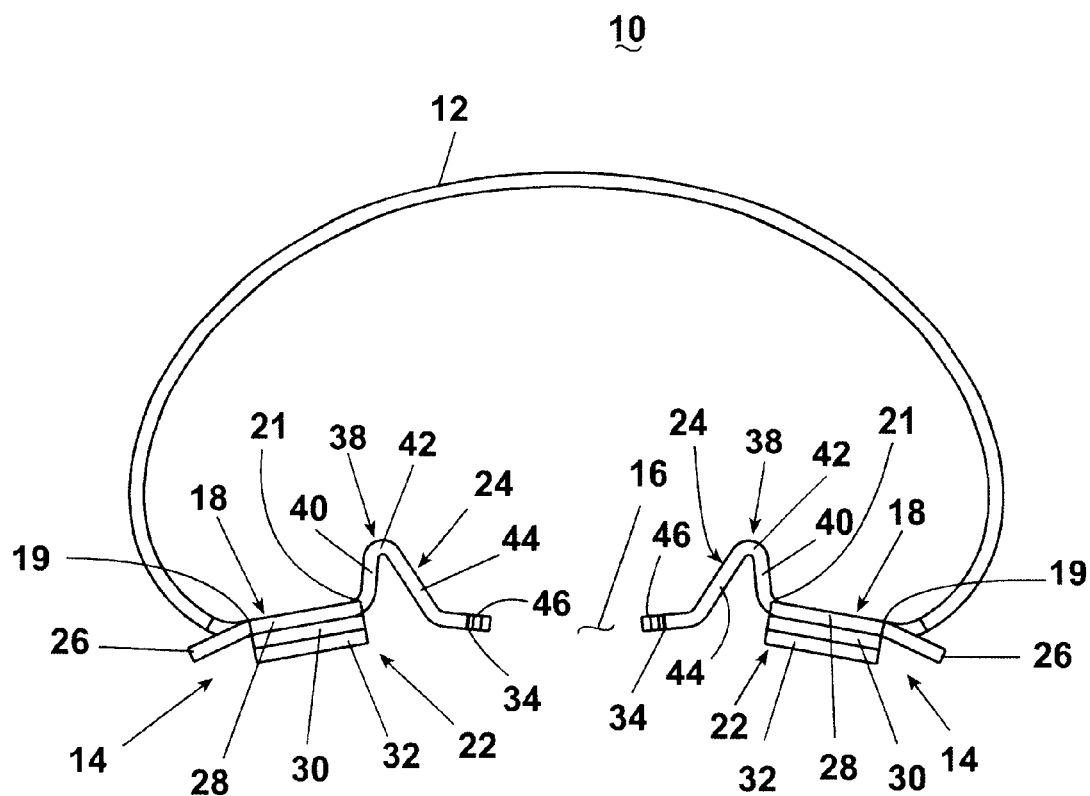
FIG. 3 is a front elevational view of the tooth clamp shown in FIG. 2.

The apertures 20 accommodate in a conventional manner a rubber dam forceps (not shown) for spreading the jaws 14 apart in order to install the clamp 10 around a tooth (not shown). The plate 18 extends forward in a generally lateral direction from the end of the bridge 12. The outward edge 19 of the plate 18 terminates in a generally laterally disposed dam engaging wing 26. The inward edge 21 of each plate 18 defines the space 16. Referring to FIG. 3, the wing 26 is bent slightly downwardly from the top of the plate 18. The dam tab 22 extends forwardly from the plate 18 and comprises a first segment 28 essentially coplanar with the plate 18, a second segment 30 orthogonal to the first segment 28, and a tongue 32 orthogonal to the second segment 30.

The resilient fingers 24 extend laterally from the inward edge 21 of the plate 18 into the space 16 and toward the oppositely disposed plate. Referring again to FIG. 3, the fingers 24 are formed with a crimp 38 comprising a first segment 40, an elbow 42, and a second segment 44. The ends 34 of the fingers 24 are bent in a slightly downward position relative to the top of the plate 18 so that the corner 46 contacts the tooth. The ends 34 of the fingers 24 define a curve 36 corresponding generally to the arc of a tooth along the gum line. In the preferred embodiment, at least two and no more than nine fingers are utilized depending upon the type of tooth (e.g., molar, bicuspid) to be clamped.

Figure 4:
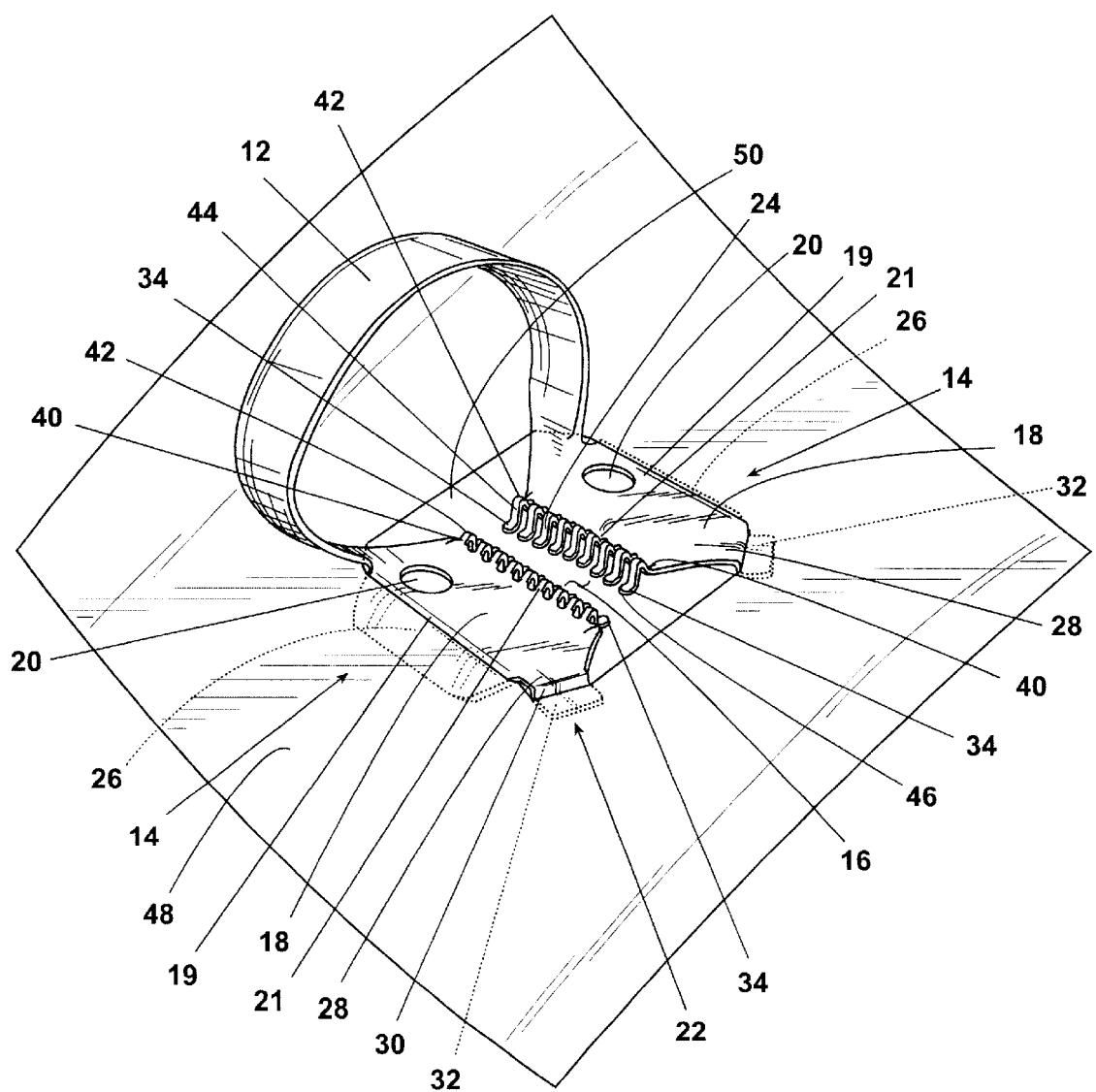
FIG. 4 is a perspective view of a tooth clamp according to the invention inserted into a hole in a rubber dam for placement around a tooth.

Referring now to FIG. 4, as with a conventional dental clamp, a rubber dam 48 is attached to the clamp 10 by stretching the edges of a hole 50 over the wings 26. Additionally, the dam tab 22 is inserted into the hole 50 to further spread the edges of the hole 50 apart and increase the size of the hole formed by the hole 50. Using conventional rubber dam forceps (not shown), the clamp 10 is placed over the selected tooth (not shown), thereby positioning the rubber dam 48 in place. The fingers 24 contact the periphery of the tooth at the corners 46 and deform individually to distribute the contact force exerted by the jaws 14 uniformly along the tooth. The slightly downward orientation of the finger ends 34 resists slippage of the clamp 10 upward and off the tooth.

While the invention has been specifically described in connection with certain specific embodiments thereof, it is to be understood that this is by way of illustration and not of limitation, and the scope of the appended claims should be construed as broadly as the prior art will permit.

What is claimed is:

1. In a dental clamp for clamping a tooth and supporting a flexible sheet around the tooth during a dental operation, the dental clamp comprising a resilient member connecting oppositely disposed jaws and biasing the jaws toward each other, the improvement comprising:

a plurality of resilient fingers extending from each jaw toward the oppositely disposed jaw.

2. A dental clamp according to claim 1 wherein the resilient fingers are arranged in a rank on each jaw.

3. A dental clamp according to claim 2 wherein the resilient fingers project slightly away from the resilient member.

4. A dental clamp according to claim 3 and further comprising a tab to engage and hold a flexible sheet.

5. A dental clamp according to claim 4 wherein the tab projects from each jaw.

6. A dental clamp according to claim 5 wherein each finger has a crimp to facilitate resiliency.

7. A dental clamp according to claim 6 wherein the ends of the fingers on each jaw are arranged to define a curve roughly approximating the curvature of a tooth.

8. A dental clamp according to claim 1 wherein the resilient fingers project slightly away from the resilient member.

9. A dental clamp according to claim 8 and further comprising a tab to engage and hold a flexible sheet.

10. A dental clamp according to claim 9 wherein the tab projects from each jaw.

11. A dental clamp according to claim 10 wherein each finger has a crimp to facilitate resiliency.

12. A dental clamp according to claim 11 wherein the ends of the fingers on each jaw are arranged to define a curve roughly approximating the curvature of a tooth.

13. A dental clamp according to claim 1 and further comprising a tab to engage and hold a flexible sheet.

14. A dental clamp according to claim 13 wherein the tab projects from each jaw.

15. A dental clamp according to claim 14 wherein each finger has a crimp to facilitate resiliency.

16. A dental clamp according to claim 15 wherein the ends of the fingers on each jaw are arranged to define a curve roughly approximating the curvature of a tooth.

17. A dental clamp according to claim 1 wherein each finger has a crimp to facilitate resiliency.

18. A dental clamp according to claim 17 wherein the ends of the fingers on each jaw are arranged to define a curve roughly approximating the curvature of a tooth.

19. A dental clamp according to claim 1 wherein the ends of the fingers on each jaw are arranged to define a curve roughly approximating the curvature of a tooth.

* * * * *

UNITED STATES PATENT AND TRADEMARK OFFICE
CERTIFICATE OF CORRECTION

PATENT NO. : 6,609,911 B2  Page 1 of 1
DATED : August 26, 2003
INVENTOR(S) : John E. Garrison It is certified that error appears in the above-identified patent and that said Letters Patent is hereby corrected as shown below:

<u>Title page,</u>
Item [75], Inventor, "Inventor:   John E. Garrison, 15800 Ridge La.," should be
-- Inventor:   John E. Garrison, 15800 Ridge Lane --

Signed and Sealed this

Twentieth Day of January, 2004

JON W. DUDAS
*Acting Director of the United States Patent and Trademark Office*